(12) United States Patent
Barnes et al.

(10) Patent No.: US 10,184,076 B2
(45) Date of Patent: Jan. 22, 2019

(54) INTERNAL OLEFIN SULFONATE COMPOSITION

(71) Applicant: SHELL OIL COMPANY, Houston, TX (US)

(72) Inventors: Julian Richard Barnes, Amsterdam (NL); James Laurel Buechele, Houston, TX (US); Hendrik Dirkzwager, Heemstede (NL); Willem Johan Louis Genuit, Baarn (NL); Jeremiah Michael Purcell, Fulshear, TX (US); Catherine Semien, Katy, TX (US); Carmen Geraldine Reznik, Friendswood, TX (US)

(73) Assignee: SHELL OIL COMPANY, Houston, TX (US)

( * ) Notice: Subject to any disclaimer, the term of this patent is extended or adjusted under 35 U.S.C. 154(b) by 283 days.

(21) Appl. No.: 14/772,795

(22) PCT Filed: Mar. 4, 2014

(86) PCT No.: PCT/US2014/020112
§ 371 (c)(1),
(2) Date: Sep. 4, 2015

(87) PCT Pub. No.: WO2014/137974
PCT Pub. Date: Sep. 12, 2014

(65) Prior Publication Data
US 2016/0017207 A1    Jan. 21, 2016

Related U.S. Application Data

(60) Provisional application No. 61/773,191, filed on Mar. 6, 2013.

(51) Int. Cl.
*E21B 43/16* (2006.01)
*C09K 8/58* (2006.01)
(Continued)

(52) U.S. Cl.
CPC .............. *C09K 8/58* (2013.01); *C07C 309/20* (2013.01); *C09K 8/12* (2013.01); *C09K 8/24* (2013.01);
(Continued)

(58) Field of Classification Search
CPC .. E21B 43/16; C09K 8/58; C09K 8/12; C09K 8/24; C09K 8/68; C09K 8/88; C09K 8/882
See application file for complete search history.

(56) References Cited

U.S. PATENT DOCUMENTS 4,183,867 A * 1/1980 Sekiguchi ............. C07C 303/02
562/123
4,248,793 A * 2/1981 Sekiguchi ............. C07C 303/06
562/123
(Continued)

FOREIGN PATENT DOCUMENTS

CN    102131890 A    7/2011
CN    102858907 A    1/2013
(Continued)

OTHER PUBLICATIONS

Chatzis et al.; "Correlation of capillary number relationship for sandstone"; SPE Journal; vol. 29; pp. 555-562; 1989.
(Continued)

*Primary Examiner* — Zakiya W Bates
*Assistant Examiner* — Crystal J Miller

(57) ABSTRACT

The present invention provides an internal olefin sulfonate composition, comprising water and an internal olefin sulfonate mixture having an average carbon number of at least 20, wherein the internal olefin sulfonate mixture comprises hydroxy sulfonates and alkene sulfonates in a weight ratio of
(Continued)

hydroxy sulfonates to alkene sulfonates of at least 3.25. The invention further provides a method of treating a crude oil containing formation.

14 Claims, 2 Drawing Sheets

(51) Int. Cl.
  *C09K 8/12*  (2006.01)
  *C09K 8/24*  (2006.01)
  *C09K 8/68*  (2006.01)
  *C09K 8/88*  (2006.01)
  *C07C 309/20*  (2006.01)
  *C08F 220/56*  (2006.01)
  *C08F 220/38*  (2006.01)

(52) U.S. Cl.
  CPC ............... *C09K 8/68* (2013.01); *C09K 8/882* (2013.01); *E21B 43/16* (2013.01); *C08F 220/56* (2013.01); *C08F 2220/387* (2013.01)

(56) References Cited

U.S. PATENT DOCUMENTS

| | | | | |
|---|---|---|---|---|
| 4,488,976 A * | 12/1984 | Dilgren | ............... | C09K 8/592 166/270.1 |
| 4,507,223 A * | 3/1985 | Tano | ............... | C09K 8/584 507/259 |
| 4,537,253 A | 8/1985 | Morita et al. | | |
| 4,544,033 A * | 10/1985 | Ukigai | ............... | C09K 8/584 166/270.1 |
| 4,597,879 A * | 7/1986 | Morita | ............... | C09K 8/584 166/270.1 |
| 4,852,653 A * | 8/1989 | Borchardt | ............... | C09K 8/592 166/270.1 |
| 4,979,564 A * | 12/1990 | Kalpakci | ............... | C09K 8/584 166/270.1 |
| 5,068,043 A * | 11/1991 | Thigpen | ............... | C09K 8/584 166/270.1 |
| 5,078,916 A * | 1/1992 | Kok | ............... | C11D 1/143 510/488 |
| 5,103,909 A * | 4/1992 | Morgenthaler | ............... | C09K 8/502 166/270 |
| 5,199,490 A * | 4/1993 | Surles | ............... | C09K 8/5086 166/270 |
| 5,284,206 A * | 2/1994 | Surles | ............... | C09K 8/5086 166/270 |
| 5,510,306 A * | 4/1996 | Murray | ............... | B01J 29/65 502/64 |
| 5,633,422 A * | 5/1997 | Murray | ............... | B01J 29/65 585/671 |
| 5,648,584 A * | 7/1997 | Murray | ............... | B01J 29/65 585/664 |
| 5,648,585 A | 7/1997 | Murray et al. | | |
| 5,654,261 A * | 8/1997 | Smith | ............... | C07C 51/412 507/113 |
| 5,849,960 A * | 12/1998 | Singleton | ............... | C07C 31/125 252/182.11 |
| 6,439,308 B1 * | 8/2002 | Wang | ............... | C09K 8/58 166/270 |
| 9,284,481 B2 * | 3/2016 | Barnes | ............... | C09K 8/584 |
| 9,441,148 B2 * | 9/2016 | Barnes | ............... | E21B 43/16 |
| 2008/0171672 A1 * | 7/2008 | Cano | ............... | C09K 8/584 507/227 |
| 2009/0203557 A1 * | 8/2009 | Barnes | ............... | C09K 8/584 507/259 |
| 2009/0203558 A1 * | 8/2009 | Barnes | ............... | C09K 8/58 507/277 |
| 2010/0282467 A1 * | 11/2010 | Hutchison | ............... | C07C 303/06 166/305.1 |
| 2013/0190543 A1 * | 7/2013 | Barnes | ............... | C09K 8/584 585/4 |
| 2014/0110305 A1 * | 4/2014 | Barnes | ............... | E21B 43/16 208/14 |

FOREIGN PATENT DOCUMENTS

| | | | | |
|---|---|---|---|---|
| EP | | 0351928 | 1/1990 | |
| EP | | 0377261 | 7/1990 | |
| EP | | 0482687 | 4/1992 | |
| EP | | 0830315 | 3/1998 | |
| WO | | 2011098493 | 8/2011 | |
| WO | | 2011100301 | 8/2011 | |
| WO | WO 2011098493 A1 * | | 8/2011 | ............ C09K 8/584 |
| WO | | 2012143433 | 10/2012 | |
| WO | | 2012163852 | 12/2012 | |

OTHER PUBLICATIONS

Falls, et al.: "Field Test of Cosurfactant-Enhanced Alkaline Flooding"; SPE Reservoir Engineering; pp. 217-223; Aug. 1994.
Barnes., et al.; Application of Internal Olefin Sulfonates and Other Surfactants to EOR. Part 1: Structure—Performance Relationships for Selection at Different Reservoir Conditions, SPE 129766, Apr. 24, 2010, XP055009775, the whole document.
"Why Internal Olefins are Difficult to Sulfonate"; Tenside Detergents; vol. 22, No. 4; pp. 193-195; 1985.

* cited by examiner

INTERNAL OLEFIN SULFONATE COMPOSITION

PRIORITY CLAIM

The present application is the National Stage (§ 371) of International Application No. PCT/US2014/020112, filed Mar. 4, 2014, which claims priority from U.S. Provisional Application No. 61/773,191, filed Mar. 6, 2013 incorporated herein by reference.

FIELD OF THE INVENTION

The present invention relates to an internal olefin sulfonate composition and a method of treating a crude oil containing formation.

BACKGROUND OF THE INVENTION

Hydrocarbons may be recovered from hydrocarbon-bearing formations by penetrating the formation with one or more wells. Hydrocarbons may flow to the surface through the wells. Conditions (e.g. permeability, hydrocarbon concentration, porosity, temperature, pressure, amongst others) of the hydrocarbon containing formation may affect the economic viability of hydrocarbon production from the hydrocarbon containing formation. A hydrocarbon-bearing formation may have natural energy (e.g. gas, water) to aid in mobilizing hydrocarbons to the surface of the hydrocarbon containing formation.

Natural energy may be in the form of water. Water may exert pressure to mobilize hydrocarbons to one or more production wells. Gas may be present in the hydrocarbon-bearing formation (reservoir) at sufficient pressures to mobilize hydrocarbons to one or more production wells. The natural energy source may become depleted over time. Supplemental recovery processes may be used to continue recovery of hydrocarbons from the hydrocarbon containing formation. Examples of supplemental processes include waterflooding, polymer flooding, alkali flooding, thermal processes, solution flooding or combinations thereof.

In chemical enhanced oil recovery (cEOR) the mobilization of residual oil saturation is achieved through surfactants which generate a sufficiently (ultra) low crude oil/water interfacial tension (IFT) to give a capillary number large enough to overcome capillary forces and allow the oil to flow (I. Chatzis and N. R. Morrows, "Correlation of capillary number relationship for sandstone". SPE Journal, Vol. 29, pp 555-562, (1989).

Compositions and methods for enhanced hydrocarbons recovery utilizing an alpha olefin sulfate-containing surfactant component are known. U.S. Pat. Nos. 4,488,976 and 4,537,253 describe enhanced oil or recovery compositions containing such a component. Compositions and methods for enhanced hydrocarbons recovery utilizing internal olefin sulfonates are also known. Such a surfactant composition is described in U.S. Pat. No. 4,597,879.

U.S. Pat. No. 4,979,564 describes the use of internal olefin sulfonates in a method for enhanced oil recovery using low tension viscous water flooding. An example of a commercially available material described as being useful was ENORDET IOS 1720, a product of Shell Oil Company identified as a sulfonated $C_{17-20}$ internal olefin sodium salt. This material has a low degree of branching. U.S. Pat. No. 5,068,043 describes a petroleum acid soap-containing surfactant system for waterflooding wherein a cosurfactant comprising a $C_{17-20}$ or a $C_{20-24}$ internal olefin sulfonate was used. In "Field Test of Cosurfactant-enhanced Alkaline Flooding" by Falls et al., *Society of Petroleum Engineers Reservoir Engineering*, 1994, the authors describe the use of internal olefin sulfonates in a waterflooding composition.

In WO2011100301 the use of internal olefin sulfonates is described in conjunction with viscosity reducing compounds. Similarly, Barnes, et al. (SPE-129766-PP "Application of Internal Olefin Sulfonates and Other Surfactants to EOR. Part 1: Structure—Performance Relationships for Selection at Different Reservoir Conditions", SPE Improved Oil Recovery Symposium, Tulsa, Okla., USA, 24-28 Apr. 2010) reported on the use of internal olefin sulfonate (IOS), in particular IOS 19-23 and IOS 20-24, based surfactant systems for chemical enhanced oil recovery applications. According to Barnes et al., given the potentially large volumes of surfactants that need to be manufactured and transported to the field, it is highly desirable that the surfactant active matter, i.e. the internal olefin sulfonates, be at as high concentration as possible in order to reduce transportation costs and logistical issues.

The internal olefin sulfonates may be provided in concentrated form containing typically 15 wt % or more of internal olefin sulfonates (also referred to as active matter). However, the fluids that are injected into the reservoir comprise relatively low concentrations of the internal olefin sulfonates. These fluids that are injected are prepared by diluting small amounts of the concentrated internal olefin sulfonate with water or brine and optionally other compounds. In order to tailor the enhanced oil recovery conditions for each reservoir it is important to provide an injectable fluid having a uniform composition. Consequently, the concentrated internal olefin composition used to prepare the injectable fluid is required to have a uniform composition.

Due to the nature of the composition, which comprises water as well as components with varied hydrophobic strength such as relatively more hydrophilic hydroxy sulfonates and relatively more hydrophobic alkene sulfonates, the concentrated internal olefin composition can be prone to phase separation. Such phase separation is undesired as the separate phases have a different composition, which may lead to variation in the composition of the injectable fluid that is prepared from a concentrated internal olefin composition. The tendency of a batch of internal olefin composition toward phase separation may not always be visibly detected directly following the production of the batch. It is possible that the internal olefin composition phase separates during transport to the oil production site and could be used to prepare injectable fluid having a non-uniform composition. There is a need in the art for internal olefin compositions that have an increased physical stability, i.e. that have a reduced tendency to phase separate prior to the mixing of the internal olefin composition with any other components, such as water or brine, to form the injectable fluid.

SUMMARY OF THE INVENTION

It has now been found that the physical stability of internal olefin sulfonate compositions are directly related to the ratio of hydroxy sulfonates and alkene sulfonates in the internal olefin sulfonate composition. It has been found that internal olefin sulfonate compositions, wherein this ratio exceeds a value of 3.25 have an increased physical stability, making these internal olefin sulfonate compositions particularly suitable for chemically enhanced oil recovery purposes, in particular where the oil recovery takes place at remote locations, at locations from the internal sulfonate composition production site, or where a batch of internal sulfonate composition is used over prolonged time periods to prepare injectable fluids.

Accordingly, the present invention provides an internal olefin sulfonate composition, comprising water and an internal olefin sulfonate mixture having an average carbon number of at least 20, wherein the internal olefin sulfonate mixture comprises hydroxy sulfonates and alkene sulfonates in a weight ratio of hydroxy sulfonates to alkene sulfonates of at least 3.25.

It has been found that individual components of the internal olefin sulfonate composition have an intrinsic stabilizing or destabilizing influence on the internal olefin sulfonate composition. Appropriate reaction conditions during the manufacture of the internal olefin sulfonate composition may be used to direct the reaction toward stabilizing components, preferentially over destabilizing components. The internal olefin sulfonate compositions according to the present invention show an improved tendency to remain physically stable for sufficient time to be stored and transported for use in chemically enhanced oil recovery applications. This significantly improves the compositional uniformity of fluids for injection into a reservoir prepared by diluting concentrated internal olefin sulfonate compositions with water or brine, preferably water and/or brine from the formation from which crude oil is to be extracted.

In another aspect, the invention provides a method of treating a crude oil containing formation comprising admixing at least the internal olefin sulfonate composition according to the invention with water and/or brine, preferably from the formation from which crude oil is to be extracted, to form an injectable fluid, wherein the active matter comprises in the range of from 0.05 to 1.0 wt % and then injecting the injectable fluid into the formation.

Figure 1:
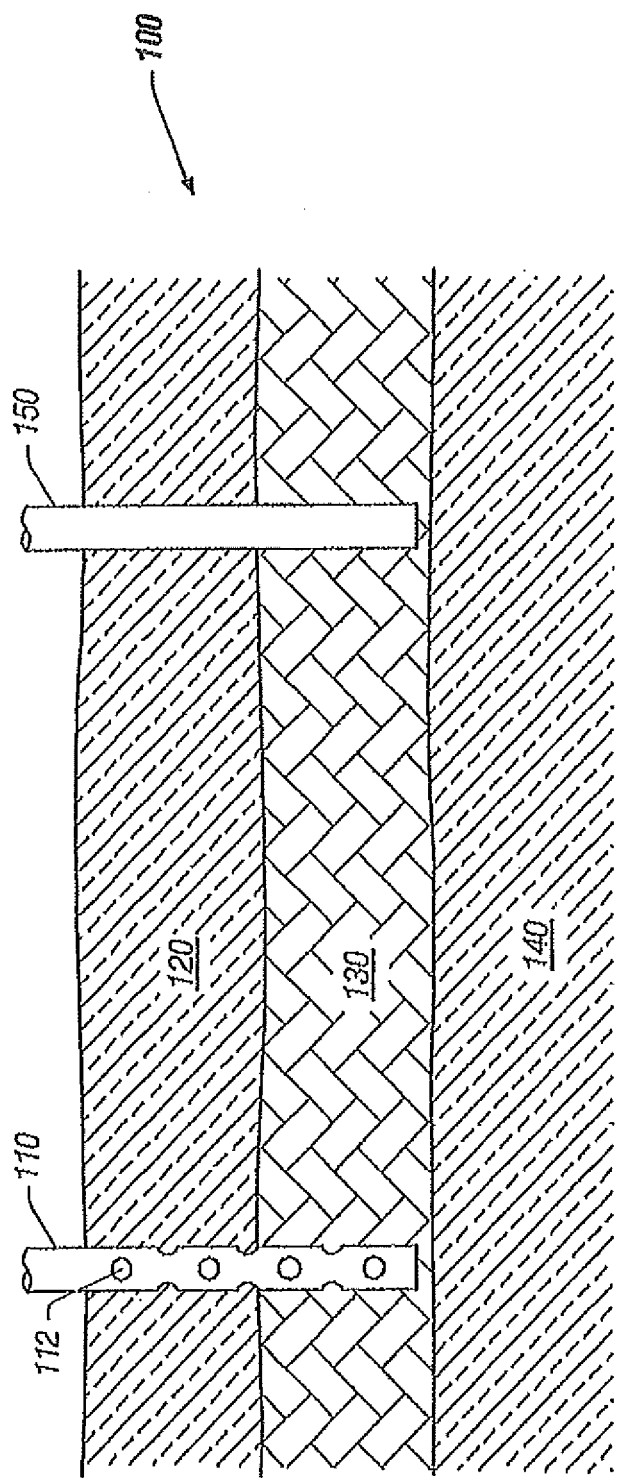
FIG. 1 depicts an embodiment of treating a hydrocarbon containing formation.

While the invention is susceptible to various modifications and alternative forms, specific embodiments thereof are shown by way of example in the drawings and will herein be described in detail. It should be understood that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Hydrocarbons may be produced from hydrocarbon formations through wells penetrating a hydrocarbon containing formation. "Hydrocarbons" are generally defined as molecules formed primarily of carbon and hydrogen atoms such as oil and natural gas. Hydrocarbons may also include other elements, such as, but not limited to, halogens, metallic elements, nitrogen, oxygen and/or sulfur. Hydrocarbons derived from a hydrocarbon formation may include, but are not limited to, kerogen, bitumen, pyrobitumen, asphaltenes, resins, saturates, naphthenic acids, oils or combinations thereof. Hydrocarbons may be located within or adjacent to mineral matrices within the earth. Matrices may include, but are not limited to, sedimentary rock, sands, silicilytes, carbonates, diatomites and other porous media.

A "formation" includes one or more hydrocarbon containing layers, one or more non-hydrocarbon layers, an overburden and/or an underburden. An "overburden" and/or an "underburden" includes one or more different types of impermeable materials. For example, overburden/underburden may include rock, shale, mudstone, or wet/tight carbonate (i.e., an impermeable carbonate without hydrocarbons). For example, an underburden may contain shale or mudstone. In some cases, the overburden/underburden may be somewhat permeable. For example, an underburden may be composed of a permeable mineral such as sandstone or limestone.

As hydrocarbons are produced from a hydrocarbon containing formation, pressures and/or temperatures within the formation may decline. Various forms of artificial lift (e.g., pumps, gas injection) and/or heating may be employed to continue to produce hydrocarbons from the hydrocarbon containing formation. Production of desired hydrocarbons from the hydrocarbon containing formation may become uneconomical as hydrocarbons are depleted from the formation.

As production rates decrease, additional methods may be employed to make a hydrocarbon containing formation more economically viable. Methods may include adding sources of water (e.g., brine, steam), gases, polymers, monomers or any combinations thereof to the hydrocarbon formation to increase mobilization of hydrocarbons.

In chemically enhanced oil recovery (cEOR) applications, surface active compounds are provided to the reservoir to improve mobilization of the hydrocarbons. A class of surface active compounds, or surfactants, that is particularly suitable for cEOR application are internal olefin sulfonates.

Internal olefin sulfonates are chemically suitable for EOR because they have a low tendency to form ordered structures/liquid crystals (which can be a major issue because long range ordered molecular structuring tends to dramatically increase fluid viscosities and can to lead decreased mobility of fluids within the hydrocarbon formations, and reduced recoveries) because they are a complex mixture of surfactants with different chain lengths. Internal olefin sulfonates show a low tendency to adsorb on reservoir rock surfaces arising from negative-negative charge repulsion between the surface and the surfactant.

The present invention provides an internal olefin sulfonate composition with an improved physical stability that can advantageously be used in cEOR applications.

In this application, "Average carbon number" as used herein is determined by multiplying the number of carbon atoms of each internal olefin sulfonate in the mixture of internal olefin sulfonates by the mole percent of that internal olefin sulfonate and then adding the products.

"Internal olefin sulfonate" as used herein means a sulfonate produced by the sulfonation of an internal olefin. The sulfonate may include mono sulfonates, disulfonates and higher sulfonates.

"active matter" as used herein means the total of mono sulfonates, disulfonates and higher sulfonates in the internal olefin composition.

"hydroxy sulfonates" as used herein includes hydroxy alkane sulfonates, but excludes any hydroxy olefin sulfonates, hydroxy di-olefin sulfonates and di-sulfonate species.

"alkene sulfonates" as used herein includes mono-olefin sulfonates, but excludes any di-sulfonate and di-olefin sulfonates species.

"$C_{19-23}$ internal olefin sulfonate" as used herein means a mixture of internal olefin sulfonates wherein the mixture has an average carbon number of from about 21 to about 23 and at least 50% by weight, preferably at least 60% by weight, of the internal olefin sulfonates in the mixture contain from 19 to 23 carbon atoms.

"$C_{20-24}$ internal olefin sulfonate" as used herein means a mixture of internal olefin sulfonates wherein the mixture has an average carbon number of from about 20.5 to about 23 and at least 50% by weight, preferably at least 65% by weight, most preferably at least 75% by weight, of the internal olefin sulfonates in the mixture contain from 20 to 24 carbon atoms.

"$C_{24-28}$ internal olefin sulfonate" as used herein means a mixture of internal olefin sulfonates wherein the mixture has an average carbon number of from 24.5 to 27 and at least 40% by weight, preferably at least 50% by weight, most preferably at least 60% by weight, of the internal olefin sulfonates in the blend contain from 24 to 28 carbon atoms.

For the purpose of defining the invention "physically stable internal olefin sulfonate composition" or "physically stable composition" as used herein refers to an internal olefin sulfonate composition or composition that does not phase separate within 1 month from the time it was produced, as determined by visual means. However, it is noted that the internal olefin sulfonate composition according to the present invention may remain physically stable for much longer periods of time.

The internal olefin sulfonate compositions according to the present invention comprise water and an internal olefin sulfonate mixture having an average carbon number of at least 20.

The internal olefin sulfonate mixture in the internal olefin sulfonate composition comprises hydroxy sulfonates and alkene sulfonates. These sulfonate compounds are typically formed during the sulfonation of internal olefins as part of the process for producing the internal olefin sulfonate composition.

In the internal olefin sulfonate composition according to the present invention the internal olefin sulfonate mixture comprises hydroxy sulfonates and alkene sulfonates in a weight ratio of hydroxy sulfonates to alkene sulfonates of at least 3.25. It has been found that such internal olefin sulfonate compositions wherein the weight ratio of hydroxy sulfonates to alkene sulfonates is at least 3.25 have significantly reduced tendency to physically separate and in most cases are fully physically stable. Consequently, the internal olefin sulfonate compositions have a reduced tendency to phase separate during storage and transport to the formation comprising hydrocarbons prior to application in a cEOR process aimed at extracting hydrocarbons from the formation. When used in cEOR, small amounts of the internal olefin sulfonate composition are mixed with, for instance, water or brine to obtain a fluid for injection into a reservoir. The composition of the injectable fluid is tailored for each reservoir and the conditions existing in that reservoir. Variations in the composition of the injectable fluid may have a negative effect on the performance of the injectable fluid. Therefore, it is highly preferably that the internal olefin sulfonate composition used to prepare the injectable fluid has to a certain degree a uniform composition, to ensure a reproducible, uniform and well defined injection fluid can be prepared. Where the internal olefin sulfonate composition has phase-separated, the formed phases will have a different composition. Resultantly, injectable fluids prepared from different phases from the same batch of internal olefin sulfonate may differ in composition.

The tendency to phase separate increases with increasing average carbon number of the internal olefin sulfonate mixture. The described stabilizing effect of the weight ratio of hydroxy sulfonates to alkene sulfonates in the internal olefin sulfonate mixture becomes significant at an average carbon number of the internal olefin sulfonate mixture of at least 20 and particularly at an average carbon number of the internal olefin sulfonate of at least 21. Preferably, the average carbon number of the internal olefin sulfonate mixture is below 35. Above an average carbon number of the internal olefin sulfonate mixture of 35, the effect of the described weight ratio of hydroxy sulfonates to alkene sulfonates in the internal olefin sulfonate mixture becomes less significant.

Preferably, the weight ratio of hydroxy sulfonates to alkene sulfonates in the internal olefin sulfonate mixture is at least 3.50. It has been found that at a weight ratio of 3.50 or more the composition is physically stable. More preferably the weight ratio of hydroxy sulfonates to alkene sulfonates in the internal olefin sulfonate mixture is at least 3.70, even more preferably 3.90, still more preferably 4.00, still even more preferably 4.50. As mentioned above, both hydroxy sulfonates and alkene sulfonates are formed during the sulfonation of internal olefins, therefore for practical reasons the upper limit for the weight ratio of hydroxy sulfonates to alkene sulfonates in the internal olefin sulfonate mixture is no more than 20.

Preferred internal olefin sulfonate compositions are compositions that comprise low amounts of disulfonates. Disulfonates may be formed as a byproduct during the sulfonation of internal olefins. A low disulfonate content in the internal olefin sulfonate composition may improve the physical stability. Although, the presence of disulfonates cannot be avoided, particularly suitable and preferred internal olefin sulfonate compositions are those, wherein the internal olefin sulfonate mixture further comprises disulfonate compounds in an amount equal to or less than 1.4 wt %, based on the weight of the internal olefin sulfonate mixture. More preferably, the internal olefin sulfonate mixture further comprises disulfonate compounds in an amount equal to or less than 1.0 wt %, even more preferably 0.60 wt %, based on the weight of the active matter. As mentioned above, disulfonates are formed during the sulfonation of internal olefins, therefore for practical reasons the lower limit for disulfonates in the internal olefin sulfonate mixture is preferably no less than 0.0005 wt %, based on the weight of the active matter.

Preferred internal olefin sulfonate compositions are compositions that comprise low amounts of diolefins sulfonates. Diolefins sulfonates may be formed as a byproduct during the sulfonation of internal mono-olefins or by sulfonation of diolefins in the olefin feedstock. A low diolefins sulfonates content in the internal olefin sulfonate composition may improve the physical stability. Although, the presence of diolefins sulfonates cannot be avoided, particularly suitable and preferred internal olefin sulfonate compositions are those, wherein the internal olefin sulfonate mixture further comprises diolefins sulfonates compounds in an amount equal to or less than 1.1 wt %, based on the weight of the active matter. More preferably, the internal olefin sulfonate mixture further comprises diolefins sulfonates compounds in an amount equal to or less than 1.0 wt %, even more preferably 0.60 wt %, based on the weight of the active matter. As mentioned above, diolefins sulfonates are formed during the sulfonation of internal olefins, therefore for practical reasons the lower limit for diolefins sulfonates in the internal olefin sulfonate mixture is preferably no less than 0.0005 wt %, based on the weight of the active matter.

Further preferred internal olefin sulfonate compositions are compositions that comprise low amounts of inorganic sulfides. Inorganic sulfides may be formed as a byproduct during a neutralization step following the sulfonation of internal olefins. A low inorganic sulfide content in the internal olefin sulfonate composition may improve the physical stability. Although, the presence of inorganic sulfides cannot be avoided, particularly suitable and preferred internal olefin sulfonate compositions are those, wherein the internal olefin sulfonate composition further comprises inorganic sulfides compounds in an amount equal to or less than 10 wt %, preferably less than 5 wt %, based on the weight of the internal olefin sulfonate mixture. More preferably, the internal olefin sulfonate mixture further comprises inorganic sulfides compounds in an amount equal to or less than 4 wt %, based on the weight of the internal olefin sulfonate mixture. As mentioned above, inorganic sulfides are formed during the neutralization step following the sulfonation of internal olefins, therefore for practical reasons the lower limit for inorganic sulfides in the internal olefin sulfonate composition is no less than 0.0001 wt %, based on the weight of the internal olefin sulfonate mixture.

In a preferred embodiment of the invention, the internal olefin sulfonate composition comprises a C20-24 internal olefin sulfonate.

In a further preferred embodiment of the invention, the internal olefin sulfonate composition comprises a C24-28 internal olefin sulfonate.

In another preferred embodiment of the invention, the internal olefin sulfonate composition comprises a C19-23 internal olefin sulfonate.

Each of the above mentioned embodiments of the invention comprising different internal olefin sulfonate mixtures may be suitable for different reservoirs and different reservoir conditions. In some cases it maybe preferred to use an internal olefin sulfonate composition comprising two or more internal olefin sulfonate mixtures selected from the group of C19-23 internal olefin sulfonate, C20-24 internal olefin sulfonate and C24-28 internal olefin sulfonate.

The internal olefin sulfonate composition preferably comprises a high active matter content. As mentioned herein above, a high active matter content allows for lower storage and transport cost. The internal olefin sulfonate composition having a high active matter content may be diluted to form the injectable liquid. Preferably, the internal olefin sulfonate composition has a concentration of active matter in the range of from 15% to 95%, preferably of from 30 to 95 wt %.

As the active matter content of the internal olefin sulfonate composition increases so does the viscosity of the internal olefin sulfonate composition. Therefore, it is preferred that the internal olefin sulfonate composition has a concentration of active matter in the range of from 15% to 35%, more preferably of from 30 to 35 wt %. With increasing viscosity, in particular above a concentration of active matter in the range of 50 wt % the phase separation becomes less visible and more difficult to detect visually.

The internal olefin sulfonate composition may also comprise a viscosity reducing compound. This compound can be any compound that lowers the viscosity of the internal olefin sulfonate composition, but it is preferably a compound that lowers the viscosity such that the composition can be transported, pumped and injected into the hydrocarbon containing formation.

The viscosity reducing compound may be a non-ionic surfactant, an alcohol, an alcohol ether, or mixture thereof. The viscosity reducing compound is preferably a $C_2$-$C_{12}$ alcohol, a $C_2$-$C_{12}$ ethoxylated alcohol, 2-butoxy ethanol, diethylene glycol butyl ether, or a mixture thereof. The viscosity reducing compound may be selected from the group consisting of ethanol, iso-butyl alcohol, sec-butyl alcohol, 2-butoxy ethanol, diethylene glycol butyl ether and mixtures thereof.

Preferably, the internal olefin sulfonate composition has a kinematic viscosity as determined by ASTM D445 at 26.7° C. (80° F.) and 20 wt % active matter, based on the internal olefin sulfonate composition, of no more than 1000 mm$^2$/s.

The internal olefin sulfonate composition may include further compounds such as, but is not limited to, organic solvents, alkyl sulfonates, aryl sulfonates, brine or combinations thereof. Organic solvents include, but are not limited to, methyl ethyl ketone, acetone, lower alkyl cellosolves, lower alkyl carbitols or combinations thereof. Some of these compounds are formed during the reaction process, others may be added to improve the behavior of the composition in hydrocarbon containing formations which contain crude oil. Where the internal olefin sulfonate composition is intended to be used for recovering hydrocarbons from hydrocarbon containing formations it may also be referred to as a hydrocarbon recovery composition.

The internal olefin sulfonate composition may be prepared by an internal olefin sulfonation process. An internal olefin is an olefin whose double bond is located anywhere along the carbon chain except at a terminal carbon atom. A linear internal olefin does not have any alkyl, aryl, or alicyclic branching on any of the double bond carbon atoms or on any carbon atoms adjacent to the double bond carbon atoms. Typical commercial products produced by isomerization of alpha olefins are predominantly linear and contain a low average number of branches per molecule.

The internal olefins that are used to make the internal olefin sulfonates of the present invention may be made by skeletal isomerization. Suitable processes for making the internal olefins include those described in U.S. Pat. Nos. 5,510,306, 5,633,422, 5,648,584, 5,648,585, 5,849,960, and European Patent EP 0830315 B1, all of which are herein incorporated by reference in their entirety. A hydrocarbon stream comprising at least one linear alpha-olefin is contacted with a suitable catalyst, such as the catalytic zeolites described in the aforementioned patents, in a vapor phase at a suitable reaction temperature, pressure, and space velocity. Generally, suitable reaction conditions include a temperature of about 200 to about 650° C., an olefin partial pressure of above about 0.5 atmosphere, and a total pressure of about 0.5 to about 10.0 atmospheres or higher. Preferably, the internal olefins of the present invention are made at a temperature in the range of from about 200 to about 500° C. at an olefin partial pressure of from about 0.5 to 2 atmospheres.

It is generally known that internal olefins are more difficult to sulfonate than alpha olefins (see "Tenside Detergents" 22 (1985) 4, pp. 193-195). In the article entitled "Why Internal Olefins are Difficult to Sulfonate," the authors state that by the sulfonation of various commercial and laboratory produced internal olefins using falling film reactors, internal olefins gave conversions of below 90 percent and further they state that it was found necessary to raise the $SO_3$:internal olefin mole ratio to over 1.6:1 in order to achieve conversions above 95 percent. Furthermore, there resulting products were very dark in color and had high levels of di- and poly-sulfonated products.

U.S. Pat. Nos. 4,183,867 and 4,248,793, which are herein incorporated by reference, disclose processes which can be used to make the branched internal olefin sulfonates of the invention. They are carried out in a falling film reactor for the preparation of light color internal olefin sulfonates. The amounts of unreacted internal olefins are between 10 and 20 percent and at least 20 percent, respectively, in the processes and special measures must be taken to remove the unreacted internal olefins. The internal olefin sulfonates containing between 10 and 20 percent and at least 20 percent, respectively, of unreacted internal olefins must be purified before being used. Consequently, the preparation of internal olefin sulfonates having the desired light color and with the desired low free oil content offer substantial difficulty.

Such difficulties can be avoided by following the process disclosed in European Patent EP 0351928 B1, which is herein incorporated by reference.

A process which can be used to make internal olefin sulfonates for use in the present invention comprises reacting in a film reactor an internal olefin as described above with a sulfonating agent in a mole ratio of sulfonating agent to internal olefin of 1:1 to 1.5:1 while cooling the reactor with a cooling means having a temperature not exceeding 60° C., directly neutralizing the obtained reaction product of the sulfonating step and, without extracting the unreacted internal olefin, hydrolyzing the neutralized reaction product.

In the preparation of the sulfonates derived from internal olefins, the internal olefins are reacted with a sulfonating agent, which may be sulfur trioxide, sulfuric acid, or oleum, with the formation of beta-sultone and some alkane sulfonic acids. The film reactor is preferably a falling film reactor.

The reaction products are neutralized and hydrolyzed. Under certain circumstances, for instance, aging, the beta-sultones are converted into gamma-sultones which may be converted into delta-sultones. After neutralization and hydrolysis, gamma-hydroxy sulfonates and delta-hydroxy sulfonates are obtained. A disadvantage of these two sultones is that they are more difficult to hydrolyze than beta-sultones. Thus, in most embodiments it is preferable to proceed without aging. The beta sultones, after hydrolysis, give beta-hydroxy sulfonates.

The cooling means, which is preferably water, has a temperature not exceeding 60° C., especially a temperature in the range of from 0 to 50° C. Depending upon the circumstances, lower temperatures may be used as well.

The reaction mixture is then fed to a neutralization hydrolysis unit. The neutralization/hydrolysis is carried out with a water soluble base, such as sodium hydroxide or sodium carbonate. The corresponding bases derived from potassium or ammonium are also suitable. The neutralization of the reaction product from the falling film reactor is generally carried out with excessive base, calculated on the acid component. Generally, neutralization is carried out at a temperature in the range of from 0 to 80° C. Hydrolysis may be carried out at a temperature in the range of from 100 to 250° C., preferably 130 to 200° C. The hydrolysis time generally may be from 5 minutes to 4 hours. Alkaline hydrolysis may be carried out with hydroxides, carbonates, bicarbonates of (earth) alkali metals, and amine compounds.

This process may be carried out batchwise, semi-continuously, or continuously. The reaction is generally performed in a falling film reactor which is cooled by flowing a cooling means at the outside walls of the reactor. At the inner walls of the reactor, the internal olefin flows in a downward direction and is contacted with the sulfonation agent, preferably sulfur trioxide. Sulfur trioxide is diluted with a stream of nitrogen, air, or any other inert gas into the reactor. The concentration of sulfur trioxide generally is between 2 and 5 percent by volume based on the volume of the carrier gas.

In the preparation of internal olefin sulfonates derived from the olefins of the present invention, it is required that in the neutralization hydrolysis step very intimate mixing of the reactor product and the aqueous base is achieved. This can be done, for example, by efficient stirring or the addition of a polar cosolvent (such as a lower alcohol) or by the addition of a phase transfer agent.

Typical internal olefin sulfonate compositions comprise in the range of from 15 to 35%, preferably 30 to 35 wt % of active matter (the internal olefin sulfonate) in water, however, if desired that less water can be added to increase the active matter content.

Following, the preparation of the internal olefin sulfonate composition, the weight ratio of hydroxy sulfonates to alkene sulfonates in the internal olefin sulfonate composition may be determined via Mass Spectrometry. Where it is observed that the weight ratio of hydroxy sulfonates to alkene sulfonates is too low, the process conditions may be adapted to increase the weight ratio. The hydroxy sulfonates and alkene sulfonates compounds may be related directly to the product yield from sulfonation, neutralization and hydrolysis conditions and thus may be controlled by changing these condition. In particular, the temperature at which the sulfonating agent is contacted with the internal olefin and the contact time between the internal olefin and the sulfonating agent may be varied to improve the weight ratio of hydroxy sulfonates to alkene sulfonates.

Following the preparation, the internal olefin sulfonate composition is typically stored and transported from the point of manufacture to the location of the hydrocarbon containing formation. The internal olefin sulfonate compositions of the present invention have the advantage that they remain physically stable over a period of time while being stored and transported.

As mentioned before the physically stable internal olefin sulfonate composition according to the present invention is particularly suitable to be used in cEOR applications. The internal olefin sulfonates, optionally together with other components in a hydrocarbon recovery composition, may interact with hydrocarbons in at least a portion of a hydrocarbon containing formation. Interaction with the hydrocarbons may reduce interfacial tension of the hydrocarbons with one or more fluids in the hydrocarbon containing formation. In other embodiments, internal olefin sulfonate compositions may reduce the interfacial tension between the hydrocarbons and an overburden/underburden of a hydrocarbon containing formation. Reduction of the interfacial tension may allow at least a portion of the hydrocarbons to mobilize through the hydrocarbon containing formation.

In a further aspect the invention therefore provides a method of treating a crude oil containing formation comprising admixing at least an internal olefin sulfonate composition according to the invention with water and/or brine, preferably from the formation from which crude oil is to be extracted, to form an injectable fluid, wherein the active matter comprises in the range of from 0.05 to 1.0 wt %, preferably in the range of from 0.1 to 0.8 wt % of the injectable fluid, and then injecting the injectable fluid into the formation.

The interactions between the internal olefin sulfonates and the hydrocarbons in the hydrocarbon containing formation have been described in for instance WO2011/100301, which is incorporated herein by reference. WO2011/100301 describes methods to determine the suitability of different internal olefin sulfonates composition for a particular hydrocarbon containing formation.

In an embodiment of a method to treat a hydrocarbon, preferably crude oil, containing formation, an internal olefin sulfonate composition may be provided (e.g., by injecting a fluid comprising the internal olefin sulfonate composition) into hydrocarbon containing formation 100 through injection well 110 as depicted in FIG. 1. Hydrocarbon formation 100 may include overburden 120, hydrocarbon layer 130, and underburden 140. Injection well 110 may include openings 112 that allow fluids to flow through hydrocarbon containing formation 100 at various depth levels. In certain embodiments, hydrocarbon layer 130 may be less than 1000 feet below earth's surface. In some embodiments, underburden 140 of hydrocarbon containing formation 100 may be oil wet. An overburden/underburden that is substantially coated by hydrocarbons may be referred to as "oil wet." Low salinity water may be present in hydrocarbon containing formation 100, in other embodiments.

In an embodiment, internal olefin sulfonate composition is provided to the formation containing crude oil with heavy components by admixing it with brine from the formation from which hydrocarbons are to be extracted or with fresh water. The mixture, i.e. the injectable fluid, is then injected into the hydrocarbon containing formation.

In an embodiment, the internal olefin sulfonate composition is provided to a hydrocarbon containing formation 100 by admixing it with brine from the formation. The amount of the internal olefin sulfonate in the injectable fluid may be from in the range of from 0.05 to 1.0 wt %, preferably in the range of from 0.1 to 0.8 wt %. More than 1.0 wt % could be used but this would likely increase the cost without enhancing the performance. The injectable fluid is then injected into the hydrocarbon containing formation.

The internal olefin sulfonate composition may interact with at least a portion of the hydrocarbons in hydrocarbon layer 130. The internal olefin sulfonate composition may reduce the interfacial tension between one or more fluids (e.g., water, hydrocarbons) in the formation and the underburden 140, one or more fluids in the formation and the overburden 120 or combinations thereof.

In an embodiment, an internal olefin sulfonate composition may interact with at least a portion of hydrocarbons and at least a portion of one or more other fluids in the formation to reduce at least a portion of the interfacial tension between the hydrocarbons and one or more fluids. Reduction of the interfacial tension may allow at least a portion of the hydrocarbons to form an emulsion with at least a portion of one or more fluids in the formation. An interfacial tension value between the hydrocarbons and one or more fluids may be altered by the internal olefin sulfonate composition to a value of less than 0.1 dyne/cm. In some embodiments, an interfacial tension value between the hydrocarbons and other fluids in a formation may be reduced by the hydrocarbon recovery composition to be less than 0.05 dyne/cm. An interfacial tension value between hydrocarbons and other fluids in a formation may be lowered by the internal olefin sulfonate composition to less than 0.001 dyne/cm, in other embodiments.

At least a portion of the internal olefin sulfonate composition/hydrocarbon/fluids mixture may be mobilized to production well 150. Products obtained from the production well 150 may include, but are not limited to, components of the internal olefin sulfonate composition, methane, carbon monoxide, water, hydrocarbons, ammonia, or combinations thereof. Hydrocarbon production from hydrocarbon containing formation 100 may be increased by greater than 50% after the internal olefin sulfonate composition has been added to a hydrocarbon containing formation.

In certain embodiments, hydrocarbon containing formation 100 may be pretreated with a hydrocarbon removal fluid. A hydrocarbon removal fluid may be composed of water, steam, brine, gas, liquid polymers, foam polymers, monomers or mixtures thereof. A hydrocarbon removal fluid may be used to treat a formation before an internal olefin sulfonate composition is provided to the formation. Hydrocarbon containing formation 100 may be less than 1000 feet below the earth's surface, in some embodiments. A hydrocarbon removal fluid may be heated before injection into a hydrocarbon containing formation 100, in certain embodiments. A hydrocarbon removal fluid may reduce a viscosity of at least a portion of the hydrocarbons within the formation. Reduction of the viscosity of at least a portion of the hydrocarbons in the formation may enhance mobilization of at least a portion of the hydrocarbons to production well 150. After at least a portion of the hydrocarbons in hydrocarbon containing formation 100 have been mobilized, repeated injection of the same or different hydrocarbon removal fluids may become less effective in mobilizing hydrocarbons through the hydrocarbon containing formation. Low efficiency of mobilization may be due to hydrocarbon removal fluids creating more permeable zones in hydrocarbon containing formation 100. Hydrocarbon removal fluids may pass through the permeable zones in the hydrocarbon containing formation 100 and not interact with and mobilize the remaining hydrocarbons. Consequently, displacement of heavier hydrocarbons adsorbed to underburden 140 may be reduced over time. Eventually, the formation may be considered low producing or economically undesirable to produce hydrocarbons.

In certain embodiments, injection of an internal olefin sulfonate composition after treating the hydrocarbon containing formation with a hydrocarbon removal fluid may enhance mobilization of heavier hydrocarbons absorbed to underburden 140. The internal olefin sulfonate composition may interact with the hydrocarbons to reduce an interfacial tension between the hydrocarbons and underburden 140. Reduction of the interfacial tension may be such that hydrocarbons are mobilized to and produced from production well 150. Produced hydrocarbons from production well 150 may include, in some embodiments, at least a portion of the components of the internal olefin sulfonate composition, the hydrocarbon removal fluid injected into the well for pretreatment, methane, carbon dioxide, ammonia, or combinations thereof. Adding the internal olefin sulfonate composition to at least a portion of a low producing hydrocarbon containing formation may extend the production life of the hydrocarbon containing formation. Hydrocarbon production from hydrocarbon containing formation 100 may be increased by greater than 50% after the internal olefin sulfonate composition has been added to hydrocarbon containing formation. Increased hydrocarbon production may increase the economic viability of the hydrocarbon containing formation.

Interaction of the internal olefin sulfonate composition with at least a portion of hydrocarbons in the formation may reduce at least a portion of an interfacial tension between the hydrocarbons and underburden 140. Reduction of at least a portion of the interfacial tension may mobilize at least a portion of hydrocarbons through hydrocarbon containing formation 100. Mobilization of at least a portion of hydrocarbons, however, may not be at an economically viable rate.

In one embodiment, polymers and/or monomers may be injected into hydrocarbon formation 100 through injection well 110, after treatment of the formation with a hydrocarbon recovery composition, to increase mobilization of at least a portion of the hydrocarbons through the formation. Suitable polymers include, but are not limited to, CIBA® ALCOFLOOD®, manufactured by Ciba Specialty Additives (Tarrytown, N.Y.), Tramfloc® manufactured by Tramfloc Inc. (Temple, Ariz.), and HE® polymers manufactured by Chevron Phillips Chemical Co. (The Woodlands, Tex.). Interaction between the hydrocarbons, the internal olefin sulfonate composition and the polymer may increase mobilization of at least a portion of the hydrocarbons remaining in the formation to production well 150.

The internal olefin sulfonate of the composition is thermally stable and may be used over a wide range of temperatures, typically up to temperatures as high as 140° C. The internal olefin sulfonate composition may be added to a portion of a hydrocarbon containing formation 100 that has an average temperature of above 70° C. because of the high thermal stability of the internal olefin sulfonate.

Figure 2:
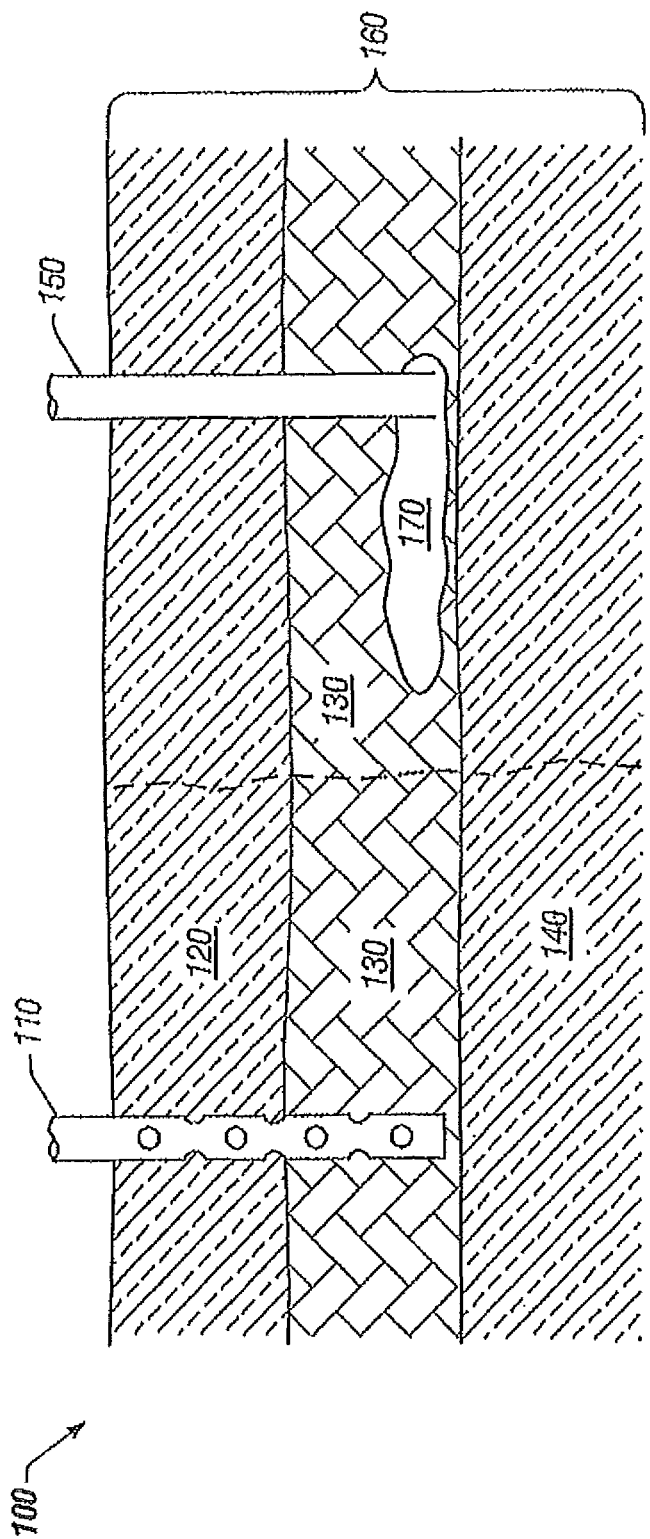
FIG. 2 depicts an embodiment of treating a hydrocarbon containing formation.

In some embodiments, an internal olefin sulfonate composition may be combined with at least a portion of a hydrocarbon removal fluid (e.g. water, polymer solutions) to produce an injectable fluid. The internal olefin sulfonate composition may be injected into hydrocarbon containing formation 100 through injection well 110 as depicted in FIG. 2. Interaction of the internal olefin sulfonate composition with hydrocarbons in the formation may reduce at least a portion of an interfacial tension between the hydrocarbons and underburden 140. Reduction of at least a portion of the interfacial tension may mobilize at least a portion of hydrocarbons to a selected section 160 in hydrocarbon containing formation 100 to form hydrocarbon pool 170. At least a portion of the hydrocarbons may be produced from hydrocarbon pool 170 in the selected section of hydrocarbon containing formation 100.

In other embodiments, mobilization of at least a portion of hydrocarbons to selected section 160 may not be at an economically viable rate. Polymers may be injected into hydrocarbon formation 100 to increase mobilization of at least a portion of the hydrocarbons through the formation. Interaction between at least a portion of the hydrocarbons, the internal olefin sulfonate composition and the polymers may increase mobilization of at least a portion of the hydrocarbons to production well 150.

In some embodiments, an internal olefin sulfonate composition may include an inorganic salt (e.g. sodium carbonate ($Na_2CO_3$), sodium hydroxide, sodium chloride (NaCl), or calcium chloride ($CaCl_2$)). The addition of the inorganic salt may help the internal olefin sulfonate composition achieve ultra-low interfacial tension. The use of an alkali (e.g., sodium carbonate, sodium hydroxide) may prevent adsorption of the IOS onto the rock surface and may create natural surfactants with components in the crude oil. The decreased interaction may lower the interfacial tension of the mixture and provide a fluid that is more mobile. The alkali may be added in an amount in the range of from 0.1 to 5 wt %.

EXAMPLES

Example 1

Several internal olefin sulfonate samples were produced having different weight ratios of hydroxy sulfonates to alkene sulfonates. All samples were produced using the same C20-24 internal olefin feedstock. The olefin was sulfonated by contacting the olefin with gaseous $SO_3$ (diluted with $N_2$) in a falling film reactor set-up. The sulfonated product was neutralized with sodium hydroxide to obtain the internal olefin sulfonate samples. The samples were sulfonated at under a variety of different temperature, $SO_3$ to olefins ratio and residence time conditions to prepare internal olefin sulfonate compositions having a wide range of hydroxy sulfonates to alkene sulfonates weight ratios.

The relative amounts of hydroxy sulfonates, alkene sulfonates and disulfonates were determined using Mass Spectrometry.

The samples were allowed to rest for a period of one month. Evaluation of the physical stability of each of the samples was based on a visual inspection. The primary visual indicator of instability of the samples is the formation of separate phases and layers in the sample. In addition, where the phase-separated samples showed a brown discoloration, the physically stable samples had uniform cream white color. The results are shown in Table 1.

TABLE 1

| Sample | Weight ratio of hydroxy sulfonate: alkene sulfonate | total disulfonate | total diolefin | Phase stability |
| --- | --- | --- | --- | --- |
| A | 6.10 | 0.13 | 0.30 | Stable |
| B | 5.47 | 0.05 | 0.11 | Stable |
| C | 5.07 | 0.75 | 0.44 | Stable |
| D | 4.38 | 0.07 | 0.98 | Stable |
| E | 4.23 | 0.58 | 0.36 | Stable |
| F | 4.12 | 0.35 | 0.35 | Stable |
| G | 3.46 | 2.87 | 0.83 | localized non-uniformity/discoloration |
| H | 3.43 | 1.34 | 0.53 | Stable |
| I | 3.40 | 2.79 | 0.98 | Stable |
| J | 3.28 | 1.36 | 0.50 | Stable |
| K | 3.25 | 1.34 | 0.53 | Stable |
| L | 3.25 | 2.40 | 1.04 | Stable |
| M* | 3.07 | 1.41 | 0.47 | Phase separation |
| N* | 2.97 | 1.71 | 0.50 | Phase separation |
| O* | 2.40 | 2.15 | 0.54 | Complete Phase separation |
| P* | 2.34 | 2.13 | 0.49 | Complete Phase separation |
| Q* | 1.62 | 2.45 | 0.98 | Phase separation |
| R* | 1.22 | 2.62 | 1.31 | Phase separation |
| Y* | 1.73 | 1.97 | 0.43 | Stable |

*Comparative examples

Samples with a weight ratio of hydroxy sulfonates to alkene sulfonates below 3.25 showed advanced to complete phase separation accompanied by significant discoloration. The samples prepared with a weight ratio of hydroxy sulfonates to alkene sulfonates between 3.25 and 3.46 and higher showed an improved physical stability. One sample (Sample G), showed some minor localized non-uniformity/discoloration, which was likely to have been caused by the high total disulfonate content. The total disulfonate content of sample G was the highest measured. The physical stability of all samples, including sample G, with a weight ratio of hydroxy sulfonates to alkene sulfonates between 3.25 and 3.46 showed a significantly improvement compared to the samples having a weight ratio of hydroxy sulfonates to alkene sulfonates below 3.25, with most of the samples being fully physically stable.

All samples having a weight ratio of hydroxy sulfonates to alkene sulfonates above 3.50 were completely physically stable.

A further comparative internal olefin sulfonate sample Y was prepared based on a mixture of internal olefins, wherein the mixture has an average carbon number of from 16 to 18 and at least 40% by weight, preferably at least 50% by weight, most preferably at least 60% by weight, of the internal olefin sulfonates in the blend contain from 15 to 18 carbon atoms.

Comparative internal olefin sulfonate sample Y, which was based on an internal olefin having an average carbon number between 16 and 18, did not show phase separation. Comparative sample Q, which has a comparable weight ratio of hydroxy sulfonates to alkene sulfonates, but is based on an internal olefin with an average carbon number above 20, was found to fully phase separate. It will be clear that the average carbon number of the internal olefin significantly influences the phase separation behavior of the resulting internal olefin sulfonate.

That which is claimed is:

1. An internal olefin sulfonate composition, comprising water and an internal olefin sulfonate mixture having an average carbon number of at least 20, wherein the internal olefin sulfonate mixture comprises hydroxy sulfonates and alkene sulfonates in a weight ratio of hydroxy sulfonates to alkene sulfonates of at least 3.25 and the internal olefin sulfonate mixture further comprises disulfonate compounds in an amount equal to or less than 1.4 wt % on an active matter basis and wherein the lower limit for disulfonates in the internal olefin sulfonate mixture is no less than 0.0005 wt %, based on the weight of the active matter wherein active matter is defined as the total of mono sulfonates, disulfonates and higher sulfonates in the internal olefin sulfonate composition.

2. The internal olefin sulfonate composition according to claim 1, wherein the internal olefin sulfonate mixture comprises hydroxy sulfonates and alkene sulfonates in a weight ratio of hydroxy sulfonates to alkene sulfonates of at least 3.50.

3. The internal olefin sulfonate composition according to claim 1, wherein the internal olefin sulfonate composition further comprises inorganic sulfide compounds in an amount equal to or less than 5 wt % on an active matter basis.

4. The internal olefin sulfonate composition according to claim 1, wherein the internal olefin sulfonate mixture further comprises diolefin sulfonate compounds in an amount equal to or less than 1.1 wt % on an active matter basis.

5. The internal olefin sulfonate composition according to claim 1, comprising a C20-24 internal olefin sulfonate.

6. The internal olefin sulfonate composition according to claim 1, comprising a C24-28 internal olefin sulfonate.

7. The internal olefin sulfonate composition according to claim 1, comprising a C19-23 internal olefin sulfonate.

8. The internal olefin sulfonate composition according to claim 7, having a concentration of active matter of from 30% to 35%.

9. The internal olefin sulfonate composition according to claim 1, having a concentration of active matter of from 30% to 95%.

10. The internal olefin sulfonate composition according to claim 1, having a kinematic viscosity of no more than 1000 mm$^2$/s, as measured with ASTM D445 at 26.7° C. and 20 wt % active matter, based on the internal olefin sulfonate composition.

11. The internal olefin sulfonate composition according to claim 1, further comprising a viscosity reducing compound.

12. A method of treating a crude oil containing formation comprising admixing at least the internal olefin sulfonate composition according to claim 1 with water and/or brine to form an injectable fluid, wherein the active matter comprises in the range of from 0.05 to 1.0 wt % of the injectable fluid and then injecting the injectable fluid into the formation.

13. The method of treating a crude oil containing formation according to claim 12 wherein the active matter comprises in the range of from 0.1 to 0.8 wt % of the injectable fluid.

14. The method of claim 12 wherein the water and/or brine is from the formation from which the crude oil is to be extracted.

* * * * *